United States Patent [19]
Miller

[11] Patent Number: 5,843,981
[45] Date of Patent: Dec. 1, 1998

[54] METHOD FOR KILLING DUST MITES AND PREVENTING ASSOCIATED ALLERGIES

[76] Inventor: Jeffery D. Miller, 28 High Ridge Rd., Ridgefield, Conn. 06877

[21] Appl. No.: 751,906

[22] Filed: Nov. 18, 1996

Related U.S. Application Data

[63] Continuation of Ser. No. 226,176, Apr. 12, 1994, abandoned.

[51] Int. Cl.$^6$ .............................. A01N 43/38; A01N 53/00
[52] U.S. Cl. ............................................. 514/421; 514/531
[58] Field of Search ...................................... 514/421, 531

[56] References Cited

U.S. PATENT DOCUMENTS

| | | | |
|---|---|---|---|
| 4,666,940 | 5/1987 | Bischoff et al. | 514/544 |
| 4,668,666 | 5/1987 | Allan | 514/63 |
| 5,271,947 | 12/1993 | Miller et al. | 424/680 |

FOREIGN PATENT DOCUMENTS

| | | |
|---|---|---|
| 48-013534 | 2/1973 | Japan . |
| 48-013536 | 2/1973 | Japan . |
| 62-240602 A2 | 10/1987 | Japan . |

OTHER PUBLICATIONS

Anderson, I. and Wilkin, D.R., *Proc. Int. Congr. Acarol. 2*: 1034–9, 1984, Meeting Date 1982. Abstract Only.
Guirguis, M.W., et al., *Agric. Res. Rev. 55(1)*: 41–8, 1977. Abstract Only.
Incho, B.H., *Soap Chem. Spec. 2*: 37–40, 1970. Abstract Only.
Arlian, *Immunol and Allergy Clinics of N America*, 9: 339–356, 1989.
Brandt et al., *J Med Entomology*, 13: 327–331, 1976.
Colloff, *Pesticide Outlook*, 1: 3–8, 1990.
Gelber, et al., *Am Rev Resp Dis*, 147: 573–578, 1993.
Heller–Haupt et al., *J Med Entomology*, 11: 551–558, 1974.
Huss et al., *J. Allergy Clin. Immunol.* 94: 27–32, 1994.
Murray et al., *Pediatrics*, 71: 418–422, 1983.
N.I.H., Publication No. 91–3042, 1991.
Platts–Mills et al., *J Allergy Clin Immunol*, 80: 755–777, 1987.
Platts–Mills, et al., *J. Allergy Clin Immunol*, 89: 1046–1060, 1992.
Sporik et al., *New England Journal of Medicine*, 323: 502–507, 1990.
Walshaw et al., *Quart J Medicine*, 58: 199–215, 1986.
Ware, G.W. *The Pesticide Book*, Thomson Publications, Fresno, CA, 1994, pp. 26–38, 61–62.

*Primary Examiner*—Allen J. Robinson
*Attorney, Agent, or Firm*—Darby & Darby

[57] ABSTRACT

A mixture of a pyrethrin, a pyethroid, and one or more synergists is applied to dust mites in a substrate, such as carpeting, in order to kill the dust mites.

2 Claims, No Drawings

METHOD FOR KILLING DUST MITES AND PREVENTING ASSOCIATED ALLERGIES

This is a continuation of application Ser. No. 08/226,176, filed Apr. 12, 1994 now abandoned.

FIELD OF THE INVENTION

This invention pertains to a method for reducing the population of house dust mites in a soft substrate such as carpeting.

BACKGROUND OF THE INVENTION

It has been known for many years that common house dust is an important cause of asthma, rhinitis and eczema in allergic individuals. The mite *Dermatophygoides pteronyssinus* and the related mites *D. farinae, D. microceras,* and *Euroglyphus maynei* are the major sources of house dust allergen in temperate climates including the United States and Europe. (Platts-Mills, et al., *J. Allergy Clin Immunol,* 89:1046–1060, 1992.)

Dust mites are eight-legged arachnids, relatives of spiders. They live in close association with humans (or other warm-blooded animals), their main food source being the shed scales from skin. Adult mites are approximately 300 microns ($3/_{10}$ mm) in length, having developed over approximately 25 days through egg, larval and nymph stages. (Arlian, *Immunol and Allergy Clinics of N America,* 9:339–356, 1989.) Adults live for 2 to 3½ months, during which time each female can produce about 20–40 eggs. Dust mites are photophobic, living deep in carpets, pillows, mattresses upholstered furniture and other soft materials. House dust mites are present in nearly all homes in areas where the relative humidity is greater than 50% for some portion of the year, with literally millions of mites inhabiting a single carpet or bed.

Several specific mite-produced proteins that induce allergic reactions have been identified, and the chemical structure of these allergens has been defined. (Platts-Mills, et al., *J. Allergy Clin Immunol,* 89:1046–1060, 1992.) A major dust mite allergen is present in mite fecal particles. Each mite produces about 20 fecal particles per day, and more than 100,000 of them may be present in a gram of dust. These fecal particles vary from 10 to 40 microns in size, comparable to the size of pollen grains, and become airborne during domestic activities such as vacuuming carpets and making beds.

Allergy to dust mite allergens is a major cause of asthma in the U.S. and the world. (Platts-Mills et al., *J Allergy Clin Immunol,* 80:755–777, 1987.) There is a correlation between the level of exposure to house dust mite allergen in early childhood and the likelihood of the subsequent development of asthma. (Sporik et al., *New England Journal of Medicine,* 323:502–507, 1990.) In allergic children and adults, prior sensitization and subsequent exposure to dust mite allergens is a major risk factor for presentation to a hospital with an acute asthmatic attack. (Gelber, et al., *Am Rev Resp Dis,* 147:573–578, 1993.) Acute exposure to mite allergens has been shown to provoke wheezing, rhinitis, eustachian tube obstruction or eczema in sensitized patients; chronic exposure can cause the bronchial hyper-reactivity that is characteristic of asthma.

Conversely, mite allergic individuals improve when they are moved to a mite free environment, or when modifications are made in their homes to decrease dust mite allergen levels. Studies done in the homes of both childhood and adult asthmatics have shown that the use of allergen-impermeable mattress and pillow encasings and the removal of bedroom carpets are associated with a decrease in mite numbers, and a decrease in mite allergen, with a corresponding decrease in symptoms and in medication requirements. (Murray et al., *Pediatrics,* 71:418–422, 1983; Walshaw et al., *Quart J Medicine,* 58:199–215, 1986.) The effectiveness of these allergen avoidance measures is such that their use has been advised by the U.S. Dept. of Health and Human Services in their "Guidelines for the Diagnosis and Management of Asthma" (N.I.H., Publication No. 91-3042, 1991.)

Although carpets and upholstered furniture are major sites of dust mite growth, many allergic individuals are unable or unwilling to remove these from their home. Vacuum cleaning does not remove dust mites or significantly decrease mite allergen levels, and in fact actually increases the amount of airborne allergen. Trials employing vacuuming rather than removal of carpets failed to produce clinical improvement. Because of the importance of carpets and textile materials as habitats of dust mites, various chemicals have been proposed to kill mites in those locations.

Contrary to popular misconception, mites are not insects and are not even close relatives of insects. Zoologically, mites and insects are members of different sub-phyla. Mites are therefore as far removed from insects such as roaches or fleas as humans are from tongue worms or lancelets. It is therefore not surprising that many insecticides do not kill mites (Kirk-Othmer, *Encyclopedia of Chemical Technology,* John Wiley & Sons publisher, third edition, pp. 461–463) and many miticides do not kill insects. (Lidvik, *McGraw-Hill Encyclopedia of Science and Technology,* seventh edition, pp. 295–296.) Also, most miticides have been developed for agricultural use, to kill phytophagous mites which infest growing food crops or stored grain and which constitute different species. Such chemicals may have properties or modes of action different from those required for chemicals to be used on carpets or textiles in the home environment. Indoor use obviously requires that the chemicals be safe so that they can be approved for use by the appropriate regulatory authority, such as the Environmental Protection Agency (E.P.A.).

U.S. Pat. No. 4,666,940 discloses an acaricidal composition whose active ingredient is benzyl benzoate. The acaricidal substance is said to be applicable in the form of a liquid, a foam, or as a semi-aqueous pulverulent cleanser. A product containing benzyl benzoate (Acarosan™) is currently the only preparation approved by the United States E.P.A. for killing house dust mites. However, this product is expensive and its efficacy has been questioned (Huss et al., *J. Allergy Clin. Immunol.* in press, 1994.)

U.S. Pat. No. 5,271,947 discloses a method for reducing the population of dust mites in a substrate in a household environment with sodium chloride powder. This method is effective but sodium chloride is corrosive and messy.

Pyrethrins are naturally occurring, plant derived insecticides. Synthetic derivatives of these compounds, known as pyrethroids, are often more potent. Many pyrethrin- or pyrethroid-containing products are E.P.A. registered for use against insects in the home. Heller-Haupt and Busvine studied the effect of various insecticides and miticides on house dust mites, and found that although some insecticides were effective, others were not. It is thus not possible to predict which insecticides will be effective miticides. In particular, neither of the pyrethroids studied, bioallethrin and bioresmethrin, were effective miticides. (Heller-Haupt et al., *J Med Entomology,* 11:551–558, 1974.) Brandt and Arlian also studied the effect of various pesticides on house dust mites, finding little effect from the pyrethroid allethrin or from the synergist Butacide (piperonyl butoxide). (Brandt et al., *J Med Entomology,* 13:327–331, 1976.)

The English language abstract of Japanese patent application 62240602 discloses a powdery formulation containing the pyrethroid permethrin, for use as an insecticide and miticide. The abstract does not reflect the effectiveness of the product against house mites.

A product on sale in the U.K. for use on carpets, Sergeant's Dust Mite Patrol, contains the pyrethroid d-phenothrin. A product for sale in France, Acardust, contains bioallethrin and piperonyl butoxide. Although effective against mites in culture, Mulcahey found only 54–60% mortality of mites when the product was sprayed onto carpets. (Colloff, *Pesticide Outlook,* 1:3–8, 1990).

Despite advances in treatment, the morbidity and mortality from asthma are increasing, and direct costs for asthma treatment in the U.S. are now $3.6 billion per year. Since house dust mites are a major cause of asthma and other allergic conditions, there is a need in the art for a safe and effective method of killing these mites in the carpets and textiles of the indoor environment.

SUMMARY OF THE INVENTION

The present inventor has now found that contacting textile substrates such as carpeting with a mixture comprising pyrethrin, one or more pyrethroids, and two synergists, kills most of the house dust mites in the substrate.

DETAILED DESCRIPTION OF THE INVENTION

All patent applications, patents and literature cited in this specification are hereby incorporated by reference in their entirety. In the case of inconsistencies, the present disclosure will prevail.

In accordance with the present invention, it has been found that exposing a carpet containing house dust mites to a mixture of (i) pyrethrin, (ii) one or more pyrethroid, (iii) piperonyl butoxide and (iv) N-octyl bicycloheptene dicarboxamide reduces the population of live larval, nymph and adult dust mites, to a significantly greater degree than is effected by any one, two or three of these ingredients alone.

"Pyrethrin", as defined herein, encompasses Pyrethrins I and II and Cinerins I and II, which are natural products extracted from chrysanthemum flowers (Ware, G. W., *The Pesticide Book,* Thomson Publications, Fresno, Calif., 1994, page 61).

Pyrethroids are synthetic pyrethrin-like compounds, which include without limitation 2-Methyl-4-oxo-3-(2-propenyl)-2-cyclopenten-1-yl 2,2-dimethyl-3(1-methyl-1-propenyl)cyclopropanecarboxylate ("Allethrin", Fairfield American, Rutherford, N.J., designated FA); 2-Methyl-4-oxo-3-(2-propenyl)-2-cyclopenten-1-yl d-trans-2,2,-dimethyl-3-(2-methyl-1-propenyl)cyclopropanecarboxylate ("Bioallethrin", FA); (3 -Phenoxyphenyl)methyl d-cis/trans 2,2-dimethyl-3-(2-methylpropenyl) cyclopropanecarboxylate ("Phenothrin", FA); (5-Benzyl-3-furyl)methyl 2,2-dimethyl-3-(2-methylpropenyl) cyclopropanecarboxylate ("Resmethrin", FA); d-trans (5-Benzyl-3-furyl)methyl 2,2-dimethyl-3-(2-methylpropenyl)cyclopropanecarboxylate ("Bioresmethrin", FA); (1-Cyclohexane-1,2-dicarboximid) methyl 2,2,-dimethyl-3-(2-methylpropenyl) cyclopropanecarboxylate ("Tetramethrin", FA); Cyclopropanecarboxylic acid, 3-(2,2-dichloroethenyl)-2,2-dimethyl-(3-phenoxyphenyl)methyl ester ("Permethrin", FMC Corporation, Philadelphia, Pa.); Cyclopropanecarboxylic acid, 3-(2,2-dichloroethenyl)-2,2-dimethyl-cyano(3-phenoxyphenyl)methyl ester ("Cypermethrin", FMC);(2-Methyl-1,1'-biphenyl-3-yl)methyl 3-(2-chloro-3,3,3,-trifluoro-1-propenyl)-2,2-dimethylcyclopropanecarboxylate ("Bifenthrin", FMC);(2,3,5,6-Tetrafluoro-4-methylphenyl) methyl cis-3-(2-chloro-3,3,3,-trifluoro-1-propenyl)2,2,-dimethylcyclopropanecarboxylate ("Tefluthrin", ICI, Wilmington, Del.); Cyclopropanecarboxylic acid, 3-(2-chloro-3,3,3,-trifluoro-1-propenyl)-2,2-dimethyl-. cyano(3-phenoxyphenyl)methyl ester ("Lambdacyhalothrin", ICI); Benzeneacetic acid, 4-chloro-.alpha.-(1-methylethyl)-, cyano(3-phenoxyphenyl)methyl ester ("S-fenvalerate", Du Pont, Wilmington, Del.); 5-Benzyl 3-furylmethyl(+) cis-(1R,3S,E)2,2-dimethyl-3-(2-oxo-2,3,4,5-tetrahydrothiophenylidene methyl) cyclopropanecarboxylate ("Kadethrine", Roussel Uclaf, Englewood Cliffs, N.J.); 2,2-Dimethyl-3-(1,2,2,2-tetrabromoethyl) cyclopropanecarboxylic acid, cyano (3-phenoxyphenyl) methyl ester ("Tralomethrin", Hoechst-Roussel, Soverville, N.J.); Cyclopropanecarboxylic acid, 3-(2,2-dibromoethenyl)-2,2-dimethyl, cyano(3-phenoxyphenyl)methyl ester ("Deltamethrin", Rhone-Poulenc, Research Triangle Park, N.C.); Alpha-cyano-3-phenoxybenzyl 2,2,3,3,-tetramethyl cyclopropanecarboxylate ("Fenpropathrin", Valent Corporation, Walnut Creek, Calif.); N-(2-Chloro-4-trifluoromethyl) phenyl-D,L-valine (+−)-cyano (3-phenoxyphenyl) methyl ester ("Fluvalinate", Sandoz, Des Plaines, Ill.); Cyano (4-fluoro-3-phenoxyphenyl)methyl 3-1 2,2-dichloromethenyl)-2,2,-dimethylcyclopropanecarboxyalte ("Cyfluthrin", Mobay, Kansas City, Mo.); Betacyfluthrin and flumethrin (Bayer, Bayerwerk, Germany); and Acrinathrin (Roussel Uclaf, Englewood Cliffs, N.J.).

The synergists useful in the present invention fall into two groups: Group I includes without limitation piperonyl butoxide (McLaughlin Gormley King, Minneapolis, Minn., designated "MGK"), 2-(3,4-Methylenedioxyphenoxy)3,6,9-trioxaundecane ("Sesamex"), 1,2-Methylenedioxy-4-(2-(octylsulfidynyl) propyl)benzene, Dillapiol, and Sesamine; and Group II includes without limitation N-octyl bicycloheptene dicarboxamide ("MGK-264", available from MGK), N-decylimidazole and N, N-Dibutyl-p-chlorobenzenesulfonadmide ("WARF-antiresistant".)

The formulations of the present invention comprise pyrethrin in a concentration of between about 0.01% and about 1%, preferably about 0.14%; piperonyl butoxide in a concentration of between about 0.05% and about 10%, preferably 1%; N-octyl bicycloheptene dicarboxamide in a concentration of between about 0.05% and about 10%, preferably 1%; and the pyrethroid(s) in a concentration of between about 0.01% and about 1.0, preferably 0.063%.

The formulations of the present invention also optionally encompass solvents, and/or emulsifiers, and/or propellants as are commonly used in the art (Ware, pages 26–38). Solvents that may be used include oil-based solvents, water-miscible solvents, and water. Propellants include, without limitation, dimethyl ether, hydrocarbons, and nitrogen. Alternatives to liquid formulations include wettable powders and slow-release formulations.

The formulations of the present invention are applied to a carpet or textile substrate so that a sufficient amount of the mixture of compounds contacts the dust mites living therein. For liquid or sprayable formulations, a sufficient amount is one that visibly wets the carpet in that it covers it with a minimally visible film immediately upon application. Applications can be repeated as necessary, generally at intervals of two to three months, although repeat treatments at one week and one month after the first application are desirable.

The substrates encompassed by the methods of the present invention include without limitation carpets, rugs, bedding materials, upholstered furnishings, and toys made from fabrics. The environments in which these substrates are found and may be treated include homes, schools, offices, and the like.

As discussed in Example 1 below, several commercially available products contain combinations of these ingredients and such products are useful in practicing the method of the present invention. Other formulations that include these ingredients may also be used.

The present invention is further described in the following working examples, which are intended to illustrate the invention without limiting its scope.

EXAMPLE 1

Ongoing cultures of *D. Pteronyssinus* mites were maintained in TetraMin™ brand fish food (made by TetraWerke Ulrich Baensch GMBH, Germany, and distributed by Pets International, Chester Hill, NSW, Australia) in incubators maintained at 75° F. and 75% relative humidity. Fifty six sections of carpeting, approximately 7×7 cm in size and having a pile depth of 1.5 cm, were inoculated by pressing them onto the cultures and brushing the culture material in with a soft brush. Inoculated carpet sections were incubated for an additional 5 days. The following treatments were then each applied to eight sections of inoculated carpet, in the same manner as prescribed by the manufacturer for each product's known use:
Treatment A: Raid Flea Killer
Treatment B: Raid Flea Killer Plus
Treatment C: Raid House and Garden (COMPARATIVE)
Treatment D: Hartz 2 in 1 Flea and Tick Killer (COMPARATIVE)
Treatment E: Sergeant's Rug Patrol (COMPARATIVE)
Treatment F: Sergeants Dust Mite Patrol (COMPARATIVE)
Treatment G: Untreated Control Products A, B, and C are from S.C. Johnson & Son, Racine, Wis.; D is from Hartz Mountain Corp., Harrison, N.J.; E is from ConAgra Pet Products, Richmond, Va.; and F is from ConAgra Pet Products, Louth Links, UK.

The composition of each of these products as weight percentages is shown in Table 1:

TABLE 1

| Treatment | pyrethrin | tetra-methrin | d-pheno-thrin | piperonyl butoxide | N-octyl b. d. | s-meth |
|---|---|---|---|---|---|---|
| A | 0.14% | 0.063% | — | 1.0% | 0.98% | — |
| B | 0.14% | 0.063% | — | 1.0% | 1.0% | 0.15% |
| C | 0.176% | 0.081% | — | 1.0% | — | — |
| D | 0.11% | — | — | 0.22% | 0.37% | — |
| E | — | — | 0.48% | 1.63% | — | — |
| F | — | — | 0.504% | — | — | — |
| G (Untreated Control) | — | — | — | — | — | — |

Note:
N-octyl b. d. = N-octyl bicycloheptene dicarboxamide
s-meth = s-methoprene Two days later, the surfaces of the carpet sections were vacuumed to remove dead mites and food. Simple vacuuming does not, however, remove live mites from carpets. The number of live mites remaining in the carpeting after treatment was then determined by the heat escape method. Briefly, clear plastic adhesive sheets (Contact™ brand self-adhesive covering, Rubbermaid Inc.) were placed sticky side down on the top of the carpet sections, which were then placed base down on microscope slide warmer with variable surface temperature (Fischer Scientific, Inc.) and covered with opaque glass and a weight. The temperature of the heated surface was increased by about 1° C. per minute, from a room temperature of about 24° C. to about 70° C. over 45 minutes, and maintained at about 70° for an additional 15 minutes. In an attempt to escape from the heat, the mites move from their usual habitat deep in the carpet to its surface, where they stick to the adhesive sheet. The sheet was then removed and overlayed upon a clear plastic grid. The number of larval, nymph and adult mites in the central 10 cm$^2$ of each carpet section was then counted under a stereo-microscope. The mean number of surviving mites for each treatment was as follows:

| | |
|---|---|
| Treatment A: 1.5 | ($p < 0.01$) |
| Treatment B: 2.7 | ($p < 0.01$) |
| Treatment C: 42 | ($p < 0.05$) |
| Treatment D: 251 | ($p = 0.28$) |
| Treatment E: 85 | ($p = 0.19$) |
| Treatment F: 63 | ($p = 0.08$) |
| Treatment G: 148 (Control) | |

The treatments designated A and B, which are embodiments of the present invention, decreased the number of living dust mites in the carpet by more than 98%. The other treatments, using some but not all of the essential ingredients of the invention, were much less effective or were completely ineffective. Statistical analysis by t-test revealed that the results of treatments D, E, and F were not significantly different than the control, whereas the differences in treatments A and B were highly significant. Treatment C was moderately effective, but the results indicate that N-octyl bicycloheptene dicarboxamide acts as an effective miticidal synergist.

EXAMPLE 2

A section of carpeting measuring 750 cm$^2$ was inoculated with 10 cc of *D. pteonyssinus* culture, and incubated at 75° F., 75% relative humidity for 4 weeks. The carpet was cut into thirds. One section was sprayed with Raid Flea Killer (treatment A above), according to manufacturer's directions; one section was treated with Acarosan™ brand of benzyl benzoate miticide (Fisons Pharmaceuticals, Rochester, N.Y.) according to manufacturer's directions; a third served as an untreated control. Carpet sections were incubated for a further two days, after which the number of living dust mites in each 250 cm$^2$ piece was determined by the heat escape method as described in Example 1.

The number of living mites after treatment in each carpet was as follows:

| | |
|---|---|
| Raid Flea and Tick Killer: | 0 |
| Acarosan ™: | 191 |
| Untreated Control: | 939 |

Use of a single application of the first product, which is an embodiment of the present invention, was effective in completely eliminating a long-term infestation of house dust mites from the carpet sample. It was significantly more effective in this experiment than was the only product currently registered by the E.P.A. for this purpose.

What is claimed is:

1. A method for killing dust mites living in a substrate, said mites selected from the group consisting of *Dermatophagoides pteronyssinus, Dermatophagoides farinae, Dermatophagoides microceras,* and *Euroglyphus maynei,* said substrate selected from the group consisting of carpet, rugs, bedding materials, upholstery, and toys made from fabric, said method comprising applying to said dust mites or infested substrate thereof an amount effective for killing dust mites of a mixture comprising between about 0.01% and about 1% of pyrethrin, between about 0.01% and 1% of tetramethrin, and between about 0.05% and about 10% of piperonyl butoxide wherein said concentrations represent weight percentages relative to the weight of the final mixture.

2. The method of claim 1 wherein said mixture further comprises N-octylbicycloheptene dicarboxamide in a concentration between about 0.05% and about 10%.

* * * * *